(12) United States Patent
Kasai et al.

(10) Patent No.: US 8,466,135 B2
(45) Date of Patent: Jun. 18, 2013

(54) HAIR TREATMENT COMPOSITIONS

(75) Inventors: Masahiro Kasai, Shanghai (CN); Kayo Kobori, Wirral (GB)

(73) Assignee: Conopco, Inc., Englewood Cliffs, NJ (US)

( * ) Notice: Subject to any disclaimer, the term of this patent is extended or adjusted under 35 U.S.C. 154(b) by 23 days.

(21) Appl. No.: 12/679,690

(22) PCT Filed: Sep. 8, 2008

(86) PCT No.: PCT/EP2008/061874
§ 371 (c)(1),
(2), (4) Date: Mar. 24, 2010

(87) PCT Pub. No.: WO2009/040240
PCT Pub. Date: Apr. 2, 2009

(65) Prior Publication Data
US 2010/0202994 A1    Aug. 12, 2010

(30) Foreign Application Priority Data
Sep. 28, 2007    (EP) .................................. 07117502

(51) Int. Cl.
*A61K 31/585*    (2006.01)
*C12P 7/58*    (2006.01)

(52) U.S. Cl.
USPC ............. 514/175; 514/53; 132/202; 519/119; 435/137

(58) Field of Classification Search
USPC ...... 514/53, 175; 519/119; 132/202; 435/137
See application file for complete search history.

(56) References Cited

U.S. PATENT DOCUMENTS

| 2,989,365 | A | * | 6/1961 | Beacham et al. | ............... 8/127.6 |
| 6,384,079 | B1 | * | 5/2002 | Yu et al. | ......................... 514/577 |
| 6,558,697 | B2 | * | 5/2003 | Cannell et al. | ................ 424/450 |

FOREIGN PATENT DOCUMENTS

| EP | 1 685 843 | | 8/2006 |
| WO | 2004/054525 | | 7/2004 |
| WO | 2004/054526 | | 7/2004 |
| WO | 2005/084622 | | 9/2005 |
| WO | WO-2005/084622 A1 | * | 9/2005 |
| WO | WO-2005/094761 A1 | * | 10/2005 |

* cited by examiner

*Primary Examiner* — Ali Soroush
(74) *Attorney, Agent, or Firm* — Ronald A. Koatz

(57) ABSTRACT

A hair treatment composition comprising at least one lactone in combination with at least one disaccharide.

5 Claims, No Drawings

HAIR TREATMENT COMPOSITIONS

The invention relates to hair treatment compositions.

Various organic molecules and combinations thereof have been suggested for use in the treatment of dry, damaged and/or unmanageable hair.

WO 2004054526 describes hair treatment compositions for the care and repair of damaged hair, and for improving hair manageability, comprising a disaccharide, (in particular trehalose).

WO 2004054525 describes hair treatment compositions for the care and repair of damaged hair, and for improving hair manageability, comprising a disaccharide (in particular trehalose), and a diol (in particular 3-methyl-1,3-butanediol).

The present inventors have found that hair treatment compositions comprising a lactone and a disaccharide show improved efficacy in the treatment of hair.

The present invention provides a hair treatment composition according to claim 1.

The invention also provides the use of the above composition in the treatment of dry, damaged and/or unmanageable hair, especially of damaged hair.

The composition of the invention comprises at least one lactone. Examples of suitable lactones include:

(a) Aldonic Acid Lactones

Aldonic acids are polyhydroxy acids resulting from oxidation of the aldehyde group of an aldose to a carboxylic acid group, and the acid of which can be represented by the following general formula:

$$R(CHOH)_n CH(OH)COOH$$

where R is H or an alkyl group (usually H) and n is an integer from 1 to 6.

The aldonic acids form intramolecular lactones by removing one mole of water between the carboxyl group and one hydroxyl group.

The following are representative aldonic acid lactones:
2,3-dihydroxypropanoic acid lactones (glyceric acid lactone);
2,3,4-trihydroxybutanoic acid lactones (stereoisomers: erythronolactone, threonolactone);
2,3,4,5-tetrahydroxypentanoic acid lactones (stereoisomers: ribonolactone, arabinolactone, xylonolactone, lyxonolactone);
2,3,4,5,6-pentahydroxyhexanoic acid lactones (stereoisomers: allonolactone, altronolactone, gluconolactone, mannolactone, gulonolactone, idonolactone, galactonolactone, talonolactone), and
2,3,4,5,6,7-hexahydroxyheptanoic acid lactones (stereoisomers: alloheptonolactone, altroheptonolactone, glucoheptonolactone, mannoheptonolactone, guloheptonolactone, idoheptonolactone, galactoheptonolactone, taloheptonolactone).

(b) Aldaric Acid Lactones

Aldaric acids are polyhydroxy dicarboxylic acids derived from an aldose by oxidation of both terminal carbon atoms to carboxyl groups, and the acid of which can be represented by the following general formula:

$$HOOC(CHOH)_n CH(OH)COOH$$

where n is an integer from 1 to 4.

The aldaric acids form intramolecular lactones by removing one mole of water between one carboxyl group and one hydroxyl group.

The following are representative aldaric acid lactones:
2,3-dihydroxybutane-1,4-dioic acid lactones
2,3,4-trihydroxypentane-1,5-dioic acid lactoness (stereoisomers: ribarolactone, arabarolactone, xylarolactone, lyxarolactone);
2,3,4,5-tetrahydroxyhexane-1,6-dioic acid lactones (allarolactone, altrarolactone, glucarolactone, mannarolactone, gularic acid and gularolactone, idarolactone, galactarolactone, talarolactone);
2,3,4,5,6-pentahydroxyheptane-1,7-dioic acid lactones (stereoisomers: alloheptarolactone, altroheptarolactone, glucoheptarolactone, mannoheptarolactone, guloheptarolactone, idoheptarolactone, galactoheptarolactone, taloheptarolactone).

(c) Alduronic Acids

Alduronic acids are polyhydroxy acids resulting from oxidation of the alcohol group of an aldose to a carboxylic acid group, and can be represented by the following general formula:

$$HOOC(CHOH)_n CH(OH)CHO$$

where n is an integer from 1 to 4.

Many alduronic acids form intramolecular lactones by removing one mole of water between the carboxyl group and one hydroxyl group.

The following are representative alduronic acid lactones: riburonolactone; araburonolactone; xyluronolactone; lyxuronolactone; alluronolactone; altruronolactone; glucuronolactone; mannuronolactone; guluronolactone; iduronolactone; galacturonolactone; taluronolactone; allohepturonolactone; altrohepturonolactone; glucohepturonolactone; mannohepturonolactone; gulohepturonolactone; idohepturonolactone; galactohepturonolactone and talohepturonolactone.

(d) Aldobionic Acids

Aldobionic acids are also known as bionic acids, and typically include one monosaccharide chemically linked through an ether bond to an aldonic acid. Aldobionic acids may also be described as an oxidised form of a disaccharide or dimeric carbohydrate, such as lactobionic acid from lactose.

In most aldobionic acids, the carbon at position one of the monosaccharide is chemically linked to a hydroxyl group at a different position of the aldonic acid. Therefore, different aldobionic acids or stereoisomers can be formed from two identical monosaccharides and aldonic acids respectively.

As with acids (a) to (c) above, aldobionic acids have multiple hydroxyl groups attached to carbon chains.

Aldobionic acids can be represented by the following general formula:

$$H(CHOH)_m(CHOR)(CHOH)_n COOH$$

where m and n are integers independently from 0 to 7 and R is a monosaccharide.

Aldobionic acids can form intramolecular lactones by removing one mole of water between the carboxyl group and one hydroxyl group.

The following are representative aldobionic acid lactones: lactobionolactone; and isolactobionolactone; maltobionolactone; isomaltobionic acid isomaltobionolactone; cellobionolactone; gentiobionolactone; kojibionolactone; laminaribionolactone; melibionolactone; nigerobionolactone; rutinobionolactone, and sophorobionolactone.

Preferably, the lactone is a delta lactone. More preferably the lactone is selected from gluconolactone, galactonolactone, glucuronolactone, galacturonolactone, gulonolactone, ribonolactone, saccharic acid lactone, pantoyllactone, glucoheptonolactone, mannonolactone, and galactoheptonolactone.

Mixtures of any of the above-described carbohydrate-derived acids may also be used in the composition of the invention.

The total amount of lactone in hair treatment compositions of the invention generally ranges from 0.02 to 20%, preferably from 0.05 to 2%, more preferably from 0.05 to 0.8% by total weight lactone based on the total weight of the composition.

The present invention comprises a disaccharide, preferably the disaccharide comprises of pentose or hexose sugars, more preferably the disaccharide comprises of two hexose units.

Disaccharides can be either reducing or non-reducing sugars. Non-reducing sugars are preferred.

The D(+) form of the disaccharides are preferred. Particularly preferred are trehalose and cellobiose or mixtures thereof. Trehalose is the most preferred disaccharide.

The level of disaccharides present in the total formulation from 0.001 to 8 wt % of the total composition, preferably from 0.005 wt % to 5 wt %, more preferably from 0.01 to 3 wt %, most preferably from 0.05 wt % to 2 wt %.

Preferably, the composition according to the invention comprises inorganic salt.

In one preferred embodiment the inorganic salt is an alkali metal salt, preferably the alkali metal salt is a sulphate, more preferably it is sodium sulphate.

The alkali metal salt is present at a level from 0.001 wt % of the total composition, preferably from 0.05 wt %, most preferably from 0.1 wt %. The maximum level of salt is less than 10 wt %, preferably less than 7 wt %, more preferably less than 5 wt %.

In a second alternatively preferred embodiment the inorganic salt is a source of ammonium ions, preferably this is ammonium carbonate.

This second preferred inorganic salt is preferably present at a level from 0.01 wt % of the total composition, more preferably from 0.05 wt %. The maximum level of ammonium carbonate is preferably less than 10 wt %, more preferably less than 5 wt %, most preferably less than 1 wt %. It is further preferred if the level of ammonium carbonate is from 0.01 to 2.0 wt % of the total composition.

Hair treatment compositions according to the invention may suitably take the form of shampoos, conditioners, sprays, mousses, gels, waxes or lotions.

Particularly preferred product forms are shampoos, post-wash conditioners (leave-in and rinse-off) and hair treatment products such as hair oils and lotions.

Shampoo compositions of the invention are generally aqueous, i.e. they have water or an aqueous solution or a lyotropic liquid crystalline phase as their major component.

Suitably, the shampoo composition will comprise from 50 to 98%, preferably from 60 to 90% water by weight based on the total weight of the composition.

Shampoo compositions according to the invention will generally comprise one or more anionic cleansing surfactants which are cosmetically acceptable and suitable for topical application to the hair.

Examples of suitable anionic cleansing surfactants are the alkyl sulphates, alkyl ether sulphates, alkaryl sulphonates, alkanoyl isethionates, alkyl succinates, alkyl sulphosuccinates, alkyl ether sulphosuccinates, N-alkyl sarcosinates, alkyl phosphates, alkyl ether phosphates, and alkyl ether carboxylic acids and salts thereof, especially their sodium, magnesium, ammonium and mono-, di- and triethanolamine salts. The alkyl and acyl groups generally contain from 8 to 18, preferably from 10 to 16 carbon atoms and may be unsaturated. The alkyl ether sulphates, alkyl ether sulphosuccinates, alkyl ether phosphates and alkyl ether carboxylic acids and salts thereof may contain from 1 to 20 ethylene oxide or propylene oxide units per molecule.

Typical anionic cleansing surfactants for use in shampoo compositions of the invention include sodium oleyl succinate, ammonium lauryl sulphosuccinate, sodium lauryl sulphate, sodium lauryl ether sulphate, sodium lauryl ether sulphosuccinate, ammonium lauryl sulphate, ammonium lauryl ether sulphate, sodium dodecylbenzene sulphonate, triethanolamine dodecylbenzene sulphonate, sodium cocoyl isethionate, sodium lauryl isethionate, lauryl ether carboxylic acid and sodium N-lauryl sarcosinate.

Preferred anionic cleansing surfactants are sodium lauryl sulphate, sodium lauryl ether sulphate (n)EO, (where n is from 1 to 3), sodium lauryl ether sulphosuccinate(n)EO, (where n is from 1 to 3), ammonium lauryl sulphate, ammonium lauryl ether sulphate(n)EO, (where n is from 1 to 3), sodium cocoyl isethionate and lauryl ether carboxylic acid (n) EO (where n is from 10 to 20).

Mixtures of any of the foregoing anionic cleansing surfactants may also be suitable.

The total amount of anionic cleansing surfactant in shampoo compositions of the invention generally ranges from 0.5 to 45%, preferably from 1.5 to 35%, more preferably from 5 to 20% by total weight anionic cleansing surfactant based on the total weight of the composition.

Optionally, a shampoo composition of the invention may contain further ingredients as described below to enhance performance and/or consumer acceptability.

The composition can include co-surfactants, to help impart aesthetic, physical or cleansing properties to the composition.

An example of a co-surfactant is a nonionic surfactant, which can be included in an amount ranging from 0.5 to 8%, preferably from 2 to 5% by weight based on the total weight of the composition.

For example, representative nonionic surfactants that can be included in shampoo compositions of the invention include condensation products of aliphatic ($C_8$-$C_{18}$) primary or secondary linear or branched chain alcohols or phenols with alkylene oxides, usually ethylene oxide and generally having from 6 to 30 ethylene oxide groups.

Other representative nonionic surfactants include mono- or di-alkyl alkanolamides. Examples include coco mono- or di-ethanolamide and coco mono-isopropanolamide.

Further nonionic surfactants which can be included in shampoo compositions of the invention are the alkyl polyglycosides (APGs). Typically, the APG is one which comprises an alkyl group connected (optionally via a bridging group) to a block of one or more glycosyl groups. Preferred APGs are defined by the following formula:

$$RO\text{-}(G)_n$$

wherein R is a branched or straight chain alkyl group which may be saturated or unsaturated and G is a saccharide group.

R may represent a mean alkyl chain length of from about $C_5$ to about $C_{20}$. Preferably R represents a mean alkyl chain length of from about $C_8$ to about $C_{12}$. Most preferably the value of R lies between about 9.5 and about 10.5. G may be selected from $C_5$ or $C_6$ monosaccharide residues, and is preferably a glucoside. G may be selected from the group comprising glucose, xylose, lactose, fructose, mannose and derivatives thereof. Preferably G is glucose.

The degree of polymerisation, n, may have a value of from about 1 to about 10 or more. Preferably, the value of n lies from about 1.1 to about 2. Most preferably the value of n lies from about 1.3 to about 1.5.

Suitable alkyl polyglycosides for use in the invention are commercially available and include for example those materials identified as: Oramix NS10 ex Seppic; Plantaren 1200 and Plantaren 2000 ex Henkel.

Other sugar-derived nonionic surfactants which can be included in compositions of the invention include the $C_{10}$-$C_{18}$ N-alkyl ($C_1$-$C_6$) polyhydroxy fatty acid amides, such as the $C_{12}$-$C_{18}$ N-methyl glucamides, as described for example in WO 92 06154 and U.S. Pat. No. 5,194,639, and the N-alkoxy polyhydroxy fatty acid amides, such as $C_{10}$-$C_{18}$ N-(3-methoxypropyl) glucamide.

A preferred example of a co-surfactant is an amphoteric or zwitterionic surfactant, which can be included in an amount ranging from 0.5 to about 8%, preferably from 1 to 4% by weight based on the total weight of the composition.

Examples of amphoteric or zwitterionic surfactants include alkyl amine oxides, alkyl betaines, alkyl amidopropyl betaines, alkyl sulphobetaines (sultaines), alkyl glycinates, alkyl carboxyglycinates, alkyl amphoacetates, alkyl amphopropionates, alkylamphoglycinates, alkyl amidopropyl hydroxysultaines, acyl taurates and acyl glutamates, wherein the alkyl and acyl groups have from 8 to 19 carbon atoms. Typical amphoteric and zwitterionic surfactants for use in shampoos of the invention include lauryl amine oxide, cocodimethyl sulphopropyl betaine, lauryl betaine, cocamidopropyl betaine and sodium cocoamphoacetate.

A particularly preferred amphoteric or zwitterionic surfactant is cocamidopropyl betaine.

Mixtures of any of the foregoing amphoteric or zwitterionic surfactants may also be suitable. Preferred mixtures are those of cocamidopropyl betaine with further amphoteric or zwitterionic surfactants as described above. A preferred further amphoteric or zwitterionic surfactant is sodium cocoamphoacetate.

The total amount of surfactant (including any co-surfactant, and/or any emulsifier) in a shampoo composition of the invention is generally from 1 to 50%, preferably from 2 to 40%, more preferably from 10 to 25% by total weight surfactant based on the total weight of the composition.

Cationic polymers are preferred ingredients in a shampoo composition of the invention for enhancing conditioning performance.

Suitable cationic polymers may be homopolymers which are cationically substituted or may be formed from two or more types of monomers. The weight average ($M_w$) molecular weight of the polymers will generally be between 100 000 and 2 million daltons. The polymers will have cationic nitrogen containing groups such as quaternary ammonium or protonated amino groups, or a mixture thereof. If the molecular weight of the polymer is too low, then the conditioning effect is poor. If too high, then there may be problems of high extensional viscosity leading to stringiness of the composition when it is poured.

The cationic nitrogen-containing group will generally be present as a substituent on a fraction of the total monomer units of the cationic polymer. Thus when the polymer is not a homopolymer it can contain spacer non-cationic monomer units. Such polymers are described in the CTFA Cosmetic Ingredient Directory, 3rd edition. The ratio of the cationic to non-cationic monomer units is selected to give polymers having a cationic charge density in the required range, which is generally from 0.2 to 3.0 meq/gm. The cationic charge density of the polymer is suitably determined via the Kjeldahl method as described in the US Pharmacopoeia under chemical tests for nitrogen determination.

Suitable cationic polymers include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have C1-C7 alkyl groups, more preferably C1-3 alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the composition. In general secondary and tertiary amines, especially tertiary, are preferred.

Amine substituted vinyl monomers and amines can be polymerised in the amine form and then converted to ammonium by quaternization.

The cationic polymers can comprise mixtures of monomer units derived from amine- and/or quaternary ammonium-substituted monomer and/or compatible spacer monomers.

Suitable cationic polymers include, for example:
cationic diallyl quaternary ammonium-containing polymers including, for example, dimethyldiallylammonium chloride homopolymer and copolymers of acrylamide and dimethyldiallylammonium chloride, referred to in the industry (CTFA) as Polyquaternium 6 and Polyquaternium 7, respectively;
mineral acid salts of amino-alkyl esters of homo- and copolymers of unsaturated carboxylic acids having from 3 to 5 carbon atoms, (as described in U.S. Pat. No. 4,009,256);
cationic polyacrylamides (as described in WO95/22311).

Other cationic polymers that can be used include cationic polysaccharide polymers, such as cationic cellulose derivatives, cationic starch derivatives, and cationic guar gum derivatives.

Cationic polysaccharide polymers suitable for use in compositions of the invention include monomers of the formula:

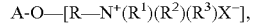

wherein: A is an anhydroglucose residual group, such as a starch or cellulose anhydroglucose residual. R is an alkylene, oxyalkylene, polyoxyalkylene, or hydroxyalkylene group, or combination thereof. $R^1$, $R^2$ and $R^3$ independently represent alkyl, aryl, alkylaryl, arylalkyl, alkoxyalkyl, or alkoxyaryl groups, each group containing up to about 18 carbon atoms. The total number of carbon atoms for each cationic moiety (i.e., the sum of carbon atoms in $R^1$, $R^2$ and $R^3$) is preferably about 20 or less, and X is an anionic counterion.

Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from the Amerchol Corporation, for instance under the tradename Polymer LM-200.

Other suitable cationic polysaccharide polymers include quaternary nitrogen-containing cellulose ethers (e.g. as described in U.S. Pat. No. 3,962,418), and copolymers of etherified cellulose and starch (e.g. as described in U.S. Pat. No. 3,958,581).

A particularly suitable type of cationic polysaccharide polymer that can be used is a cationic guar gum derivative, such as guar hydroxypropyltrimethylammonium chloride (commercially available from Rhodia in their JAGUAR trademark series). Examples of such materials are JAGUAR C13S, JAGUAR C14, JAGUAR C15 and JAGUAR C17.

Mixtures of any of the above cationic polymers may be used.

Cationic polymer will generally be present in a shampoo composition of the invention at levels of from 0.01 to 5%, preferably from 0.05 to 1%, more preferably from 0.08 to 0.5% by total weight of cationic polymer based on the total weight of the composition.

Preferably an aqueous shampoo composition of the invention further comprises a suspending agent. Suitable suspending agents are selected from polyacrylic acids, cross-linked polymers of acrylic acid, copolymers of acrylic acid with a hydrophobic monomer, copolymers of carboxylic acid-containing monomers and acrylic esters, cross-linked copolymers of acrylic acid and acrylate esters, heteropolysaccharide gums and crystalline long chain acyl derivatives. The long chain acyl derivative is desirably selected from ethylene glycol stearate, alkanolamides of fatty acids having from 16 to 22 carbon atoms and mixtures thereof. Ethylene glycol distearate and polyethylene glycol 3 distearate are preferred long chain acyl derivatives, since these impart pearlescence to the composition. Polyacrylic acid is available commercially as Carbopol 420, Carbopol 488 or Carbopol 493. Polymers of acrylic acid cross-linked with a polyfunctional agent may also be used; they are available commercially as Carbopol 910, Carbopol 934, Carbopol 941 and Carbopol 980. An example of a suitable copolymer of a carboxylic acid containing monomer and acrylic acid esters is Carbopol 1342. All Carbopol (trademark) materials are available from Goodrich.

Suitable cross-linked polymers of acrylic acid and acrylate esters are Pemulen TR1 or Pemulen TR2. A suitable heteropolysaccharide gum is xanthan gum, for example that available as Kelzan mu.

Mixtures of any of the above suspending agents may be used. Preferred is a mixture of cross-linked polymer of acrylic acid and crystalline long chain acyl derivative.

Suspending agent will generally be present in a shampoo composition of the invention at levels of from 0.1 to 10%, preferably from 0.5 to 6%, more preferably from 0.9 to 4% by total weight of suspending agent based on the total weight of the composition.

Conditioner compositions will typically comprise one or more cationic conditioning surfactants which are cosmetically acceptable and suitable for topical application to the hair.

Preferably, the cationic conditioning surfactants have the formula $N^+(R^1)(R^2)(R^3)(R^4)$, wherein $R^1$, $R^2$, $R^3$ and $R^4$ are independently ($C_1$ to $C_{30}$) alkyl or benzyl.

Preferably, one, two or three of $R^1$, $R^2$, $R^3$ and $R^4$ are independently ($C_4$ to $C_{30}$) alkyl and the other $R^1$, $R^2$, $R^3$ and $R^4$ group or groups are ($C_1$-$C_6$) alkyl or benzyl.

More preferably, one or two of $R^1$, $R^2$, $R^3$ and $R^4$ are independently ($C_6$ to $C_{30}$) alkyl and the other $R^1$, $R^2$, $R^3$ and $R^4$ groups are ($C_1$-$C_6$) alkyl or benzyl groups. Optionally, the alkyl groups may comprise one or more ester (—OCO— or —COO—) and/or ether (—O—) linkages within the alkyl chain. Alkyl groups may optionally be substituted with one or more hydroxyl groups. Alkyl groups may be straight chain or branched and, for alkyl groups having 3 or more carbon atoms, cyclic. The alkyl groups may be saturated or may contain one or more carbon-carbon double bonds (e.g., oleyl). Alkyl groups are optionally ethoxylated on the alkyl chain with one or more ethyleneoxy groups.

Suitable cationic conditioning surfactants for use in conditioner compositions according to the invention include cetyltrimethylammonium chloride, behenyltrimethylammonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, dihydrogenated tallow dimethyl ammonium chloride (e.g., Arquad 2HT/75 from Akzo Nobel), cocotrimethylammonium chloride, PEG-2-oleammonium chloride and the corresponding hydroxides thereof. Further suitable cationic surfactants include those materials having the CTFA designations Quaternium-5, Quaternium-31 and Quaternium-18. Mixtures of any of the foregoing materials may also be suitable. A particularly useful cationic surfactant for use in conditioners according to the invention is cetyltrimethylammonium chloride, available commercially, for example as GENAMIN CTAC, ex Hoechst Celanese. Another particularly useful cationic surfactant for use in conditioners according to the invention is behenyltrimethylammonium chloride, available commercially, for example as GENAMIN KDMP, ex Clariant.

Another example of a class of suitable cationic conditioning surfactants for use in the invention, either alone or in admixture with one or more other cationic conditioning surfactants, is a combination of (i) and (ii) below:
(i) an amidoamine corresponding to the general formula (I):

$$R^1CONH(CH_2)_mN\begin{matrix}R^2\\R^3\end{matrix}$$

in which $R^1$ is a hydrocarbyl chain having 10 or more carbon atoms,
$R^2$ and $R^3$ are independently selected from hydrocarbyl chains of from 1 to 10 carbon atoms, and
m is an integer from 1 to about 10; and
(ii) an acid.

As used herein, the term hydrocarbyl chain means an alkyl or alkenyl chain.

Preferred amidoamine compounds are those corresponding to formula (I) in which
$R^1$ is a hydrocarbyl residue having from about 11 to about 24 carbon atoms,
$R^2$ and $R^3$ are each independently hydrocarbyl residues, preferably alkyl groups, having from 1 to about 4 carbon atoms, and
m is an integer from 1 to about 4.

Preferably, $R^2$ and $R^3$ are methyl or ethyl groups.
Preferably, m is 2 or 3, i.e. an ethylene or propylene group.
Preferred amidoamines useful herein include stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylmine, behenamidoethyldiethylamine, behenamidoethyldimethylamine, arachidamidopropyldimethylamine, arachidamidopropyldiethylamine, arachid-amidoethyldiethylamine, arachidamidoethyldimethylamine, and mixtures thereof.

Particularly preferred amidoamines useful herein are stearamidopropyldimethylamine, stearamidoethyldiethylamine, and mixtures thereof.

Commercially available amidoamines useful herein include: stearamidopropyldimethylamine with tradenames LEXAMINE S-13 available from Inolex (Philadelphia Pa., USA) and AMIDOAMINE MSP available from Nikko (Tokyo, Japan), stearamidoethyldiethylamine with a tradename AMIDOAMINE S available from Nikko, behenamidopropyldimethylamine with a tradename INCROMINE BB available from Croda (North Humberside, England), and various amidoamines with tradenames SCHERCODINE series available from Scher (Clifton N.J., USA).

Acid (ii) may be any organic or mineral acid which is capable of protonating the amidoamine in the hair treatment composition. Suitable acids useful herein include hydrochloric acid, acetic acid, tartaric acid, fumaric acid, lactic acid, malic acid, succinic acid, and mixtures thereof. Preferably, the acid is selected from the group consisting of acetic acid, tartaric acid, hydrochloric acid, fumaric acid, and mixtures thereof.

The primary role of the acid is to protonate the amidoamine in the hair treatment composition thus forming a tertiary amine salt (TAS) in situ in the hair treatment composition. The TAS in effect is a non-permanent quaternary ammonium or pseudo-quaternary ammonium cationic surfactant.

Suitably, the acid is included in a sufficient amount to protonate all the amidoamine present, i.e. at a level which is at least equimolar to the amount of amidoamine present in the composition.

In conditioners of the invention, the level of cationic conditioning surfactant will generally range from 0.01 to 10%, more preferably 0.05 to 7.5%, most preferably 0.1 to 5% by total weight of cationic conditioning surfactant based on the total weight of the composition.

Conditioners of the invention will typically also incorporate a fatty alcohol. The combined use of fatty alcohols and cationic surfactants in conditioning compositions is believed to be especially advantageous, because this leads to the formation of a lamellar phase, in which the cationic surfactant is dispersed.

Representative fatty alcohols comprise from 8 to 22 carbon atoms, more preferably 16 to 22. Fatty alcohols are typically compounds containing straight chain alkyl groups.

Examples of suitable fatty alcohols include cetyl alcohol, stearyl alcohol and mixtures thereof. The use of these materials is also advantageous in that they contribute to the overall conditioning properties of compositions of the invention.

The level of fatty alcohol in conditioners of the invention will generally range from 0.01 to 10%, preferably from 0.1 to 8%, more preferably from 0.2 to 7%, most preferably from 0.3 to 6% by weight of the composition. The weight ratio of cationic surfactant to fatty alcohol is suitably from 1:1 to 1:10, preferably from 1:1.5 to 1:8, optimally from 1:2 to 1:5. If the weight ratio of cationic surfactant to fatty alcohol is too high, this can lead to eye irritancy from the composition. If it is too low, it can make the hair feel squeaky for some consumers.

Compositions of the invention may suitably take the form of a hair oil, for pre-wash or post-wash use. Typically, hair oils will predominantly comprise water-insoluble oily conditioning materials, such as triglycerides, mineral oil and mixtures thereof.

Compositions of the invention may also take the form of a hair lotion, typically for use in between washes. Lotions are aqueous emulsions comprising water-insoluble oily conditioning materials. Suitable surfactants can also be included in lotions to improve their stability to phase separation.

Hair treatment compositions according to the invention, particularly water-based shampoos and hair conditioners, will preferably also contain one or more silicone conditioning agents.

Particularly preferred silicone conditioning agents are silicone emulsions such as those formed from silicones such as polydiorganosiloxanes, in particular polydimethylsiloxanes which have the CTFA designation dimethicone, polydimethyl siloxanes having hydroxyl end groups which have the CTFA designation dimethiconol, and amino-functional polydimethyl siloxanes which have the CTFA designation amodimethicone.

The emulsion droplets may typically have a Sauter mean droplet diameter ($D_{3,2}$) in the composition of the invention ranging from 0.01 to 20 micrometer, more preferably from 0.2 to 10 micrometer.

A suitable method for measuring the Sauter mean droplet diameter ($D_{3,2}$) is by laser light scattering using an instrument such as a Malvern Mastersizer.

Suitable silicone emulsions for use in compositions of the invention are available from suppliers of silicones such as Dow Corning and GE Silicones. The use of such pre-formed silicone emulsions is preferred for ease of processing and control of silicone particle size. Such pre-formed silicone emulsions will typically additionally comprise a suitable emulsifier such as an anionic or nonionic emulsifier, or mixture thereof, and may be prepared by a chemical emulsification process such as emulsion polymerisation, or by mechanical emulsification using a high shear mixer. Pre-formed silicone emulsions having a Sauter mean droplet diameter ($D_{3,2}$) of less than 0.15 micrometers are generally termed microemulsions.

Examples of suitable pre-formed silicone emulsions include emulsions DC2-1766, DC2-1784, DC-1785, DC-1786, DC-1788 and microemulsions DC2-1865 and DC2-1870, all available from Dow Corning. These are all emulsions/microemulsions of dimethiconol. Also suitable are amodimethicone emulsions such as DC2-8177 and DC939 (from Dow Corning) and SME253 (from GE Silicones).

Also suitable are silicone emulsions in which certain types of surface active block copolymers of a high molecular weight have been blended with the silicone emulsion droplets, as described for example in WO03/094874. In such materials, the silicone emulsion droplets are preferably formed from polydiorganosiloxanes such as those described above. One preferred form of the surface active block copolymer is according to the following formula:

wherein the mean value of x is 4 or more and the mean value of y is 25 or more.

Another preferred form of the surface active block copolymer is according to the following formula:

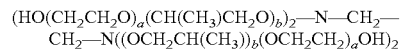

wherein the mean value of a is 2 or more and the mean value of b is 6 or more.

Mixtures of any of the above described silicone emulsions may also be used.

The above described silicone emulsions will generally be present in a composition of the invention at levels of from 0.05 to 10%, preferably 0.05 to 5%, more preferably from 0.5 to 2% by total weight of silicone based on the total weight of the composition.

A composition of the invention may contain other ingredients for enhancing performance and/or consumer acceptability. Such ingredients include fragrance, dyes and pigments, pH adjusting agents, pearlescers or opacifiers, viscosity modifiers, and preservatives or antimicrobials. Each of these ingredients will be present in an amount effective to accomplish its purpose. Generally these optional ingredients are included individually at a level of up to 5% by weight of the total composition.

Hair treatment compositions of the invention are primarily intended for topical application to the hair and/or scalp of a human subject, either in rinse-off or leave-on compositions, for the treatment of dry, damaged and/or unmanageable hair.

The invention will be further illustrated by the following, non-limiting Example, in which all percentages quoted are by weight based on total weight unless otherwise stated.

EXAMPLE

Two compositions were made following usual methods and consisted of the following active cocktails:

Cocktail A:

| | |
|---|---|
| Trehalose | 0.1% wt. |
| Ammonium carbonate | 0.5% wt. |
| Gluconolactone | 0.5% wt. |

Cocktail B:

| | |
|---|---|
| Trehalose | 0.4% wt. |
| Adipic acid | 0.1% wt. |
| Ammonium carbonate | 0.1% wt. |

Compositions comprising active cocktail A were compared against otherwise identical compositions comprising active cocktail B in a panel test.

On a 5-point scale composition A scored 4.13 for manageability of dry hair after use while composition B scored just 3.73. The scores were statistically significant.

The invention claimed is:

1. A hair treatment composition comprising 0.05 to 0.8% by wt. of an aldonic acid lactone, wherein said lactone is a 2,3,4,5,6-pentahydroxyhexanoic acid lactone selected from the group consisting of allonolactone, altronolactone, gluconolactone, mannolactone, gulonolactone, idonolactone, galactonolactone, talonolactone and mixtures thereof; and 0.05 to 2% by wt. of a disaccharide, wherein said disaccharide is trehalose.

2. A hair treatment composition according to claim 1 which is in the form of a shampoo, a post-wash conditioner (leave-in or rinse-off), a hair oil or a hair lotion.

3. A hair treatment composition according to claim 1 comprising an inorganic salt.

4. A hair treatment composition according to claim 3 wherein the salt is an alkali-metal or ammonium salt.

5. A hair treatment composition according to claim 3 wherein the salt is a carbonate or sulphate salt.

* * * * *